(12) United States Patent
Kravis

(10) Patent No.: US 7,092,485 B2
(45) Date of Patent: Aug. 15, 2006

(54) X-RAY INSPECTION SYSTEM FOR DETECTING EXPLOSIVES AND OTHER CONTRABAND

(75) Inventor: Scott D. Kravis, West Caldwell, NJ (US)

(73) Assignee: Control Screening, LLC, Fairfield, NJ (US)

( * ) Notice: Subject to any disclaimer, the term of this patent is extended or adjusted under 35 U.S.C. 154(b) by 12 days.

(21) Appl. No.: 10/444,492

(22) Filed: May 27, 2003

(65) Prior Publication Data

US 2006/0140340 A1    Jun. 29, 2006

(51) Int. Cl.
G01N 23/04    (2006.01)
G01N 23/201    (2006.01)

(52) U.S. Cl. .............................. 378/57; 378/88; 378/90

(58) Field of Classification Search .................. 378/57, 378/86, 88–90
See application file for complete search history.

(56) References Cited

U.S. PATENT DOCUMENTS

| | | | |
|---|---|---|---|
| 4,754,469 A | | 6/1988 | Harding et al. ............... 378/88 |
| 4,754,496 A | | 6/1988 | Fishkin et al. ................. 455/67 |
| 5,007,072 A | * | 4/1991 | Jenkins et al. ................ 378/88 |
| 5,060,249 A | * | 10/1991 | Eisen et al. .................... 378/57 |
| 5,231,652 A | | 7/1993 | Harding ......................... 378/86 |
| 5,265,144 A | | 11/1993 | Harding et al. ............... 378/86 |
| 5,394,453 A | * | 2/1995 | Harding ......................... 378/86 |
| 5,600,700 A | * | 2/1997 | Krug et al. .................... 378/57 |
| 5,910,973 A | | 6/1999 | Grodzins ....................... 378/57 |
| 6,118,850 A | * | 9/2000 | Mayo et al. ................... 378/83 |
| 6,122,344 A | | 9/2000 | Beevor .......................... 378/88 |
| 6,192,104 B1 | | 2/2001 | Adams et al. ................. 378/90 |
| 6,442,233 B1 | * | 8/2002 | Grodzins et al. ............. 378/57 |
| 6,532,276 B1 | | 3/2003 | Hartick et al. ................ 378/88 |
| 6,542,574 B1 | | 4/2003 | Grodzins ....................... 378/57 |
| 6,563,906 B1 | * | 5/2003 | Hussein et al. ............... 378/89 |
| 2003/0016783 A1 | | 1/2003 | Grodzins et al. ............. 378/57 |

OTHER PUBLICATIONS

Bertin, Eugene P. "Introduction to X-ray Spectrometric Analysis"□□ Plenum Press, New York. 1978, pp. 68-73.*

* cited by examiner

*Primary Examiner*—Edward J. Glick
*Assistant Examiner*—Thomas R. Artman
(74) *Attorney, Agent, or Firm*—Ernest D. Buff & Associates LLC; Ernest D. Buff; Gordon E. Fish

(57) ABSTRACT

A baggage scanning system and method employ combined angular and energy dispersive x-ray scanning to detect the presence of a contraband substance within an interrogation volume of a baggage item. The interrogation volume is illuminated with penetrating, polychromatic x-rays in a primary fan beam from a source such as a tungsten-anode x-ray tube. An energy-dependent absorption correction is determined from measurement of the attenuation of the fan beam at a plurality of different energies. Radiation coherently scattered by substances in the interrogation volume is detected by an energy-resolved x-ray detector operated at a plurality of scattering angles to form a plurality of scattering spectra. Each scattering spectrum is corrected for energy-dependent absorption and the corrected spectra are combined to produce a scattering pattern. The experimental scattering pattern is compared with reference patterns that uniquely characterize known contraband substances. The system and method can locate and identify a wide variety of contraband substances in an accurate, reliable manner. The system provides for automated screening, with the result that vagaries of human performance are virtually eliminated. False alarms and the need for hand inspection are reduced and detection efficacy is increased.

26 Claims, 10 Drawing Sheets

X-RAY INSPECTION SYSTEM FOR DETECTING EXPLOSIVES AND OTHER CONTRABAND

BACKGROUND OF THE INVENTION

1. Field of the Invention

This invention relates to the field of scanner apparatus and methods; and more particularly to inspection systems that scan luggage and cargo to detect explosives or other contraband materials therein.

2. Description of the Prior Art

In recent years, the prevalence of criminal activity that entails transportation of weapons and contraband materials has been a significant public concern. It has thus become vital to develop systems for detecting the presence of these materials, both being shipped in luggage or cargo and being carried by an individual. Of particular concern is the need to detect items used as weapons by terrorists, including ordinary firearms and knives, items such as explosive or incendiary substances, and materials which present biological, chemical or radiological hazards to people and property. The detection of illicit drugs and narcotics being transported is also of concern.

The detection of contraband in the context of air and rail transportation is especially challenging, given the need to examine large numbers of people and articles of luggage and cargo within acceptable limits on throughput and intrusiveness. Although physical inspection is a widely practiced and important technique, it is slow, cumbersome, labor intensive, and dependent on the alertness and vigilance of the inspector.

Automated systems that screen for contraband have been sought for many years. Various techniques have been proposed to detect contraband objects and materials either directly or indirectly. Magnetometry is widely used, and is sometime effective in detecting metallic objects carried by persons, but is not suited for screening cargo, which legitimately may contain large amounts of metal. Nuclear techniques, including x-ray, gamma-ray, neutron activation, and nuclear magnetic resonance methods, are applicable for screening inanimate objects. In some cases, they are able to detect metallic objects, including weapons and ancillary devices such as wires, power supplies, batteries, and triggering mechanisms for explosive devices. However, there increasingly exist threats posed by explosives associated with largely non-metallic objects, which the aforementioned methods are less able to detect. The advent of modern plastic explosives presents an especially significant threat. Even a modest, readily concealable amount of these substances can cause a substantial explosion. Moreover, miscreants have become increasingly adept at disguising weapons and explosive devices as ordinary, innocuous objects. As a result, more refined indirect methods for detection of explosives are urgently sought.

The most widely deployed methods to detect bulk quantities of explosives in luggage employ x-ray examination. The methods generally fall into two categories, viz. dual energy transmission imaging and computed tomography (CT) methods. However, both have inherent problems that limit their usefulness and effectiveness.

In the dual energy transmission method, luggage typically is scanned using a collimated x-ray fan beam of broad spectral range emanating from a Bremsstrahlung source. The x-rays transmitted through the luggage are first detected by a detector that is sensitive to low energy x-rays but passes high energy x-rays. A filter usually follows and serves to attenuate any remaining low energy x-rays. A second detector detects the transmitted high energy x-rays. Thus the data are separated into two broad energy bins. From these data it is possible to obtain an average atomic number of what is being inspected, since the relative attenuation of low and high energy x-rays depends on the atomic number of the material. For example, a low atomic number object (typically an organic substance) will have a fairly flat response to the x-ray spectrum under consideration; whereas a higher atomic number object (typically inorganic/metal) object will preferentially attenuate the low energy x-rays over high energy x-rays.

However, the dual energy transmission method has significant limitations that restrict its efficacy in detecting contraband items. These limitations include: 1) the limited accuracy with which the average atomic number can be determined; 2) the similarity in average atomic number of many common explosives and ordinarily carried, benign objects; and 3) the physical juxtaposition of materials in the luggage, which consequentially permits only an overall average atomic number to be obtained. As a result, baggage scanning systems in present use give undesirably high false alarm rates when operated with detection thresholds that are sufficiently sensitive to reliably identify actual contraband. The high false alarm rate, in turn, drives a requirement for extensive hand searching of luggage. The added scrutiny subjects passengers to discomfort and inconvenience and results in frequent passenger delays and disruption of schedules of airlines and the like. The incidence of false alarms also is likely to result in complacency and inattention on the part of security personnel.

The computed tomography method is a technique akin to methods commonly used for medical imaging. The CT method comprises collection of x-ray transmission data from a large number of angles to produce data slices of the object to be imaged. The data slices are then reconstructed, usually using a computer, to create images in which overlying objects can be distinguished. In a CT baggage scanning system the differences in measured x-ray attenuation by these different objects are used to infer their respective material densities. Upon detection of objects having densities at least similar to those of known explosive materials, security personnel are alerted to the need for follow-up inspection. Although CT theoretically can separate overlapping objects and determine their densities, a large number of benign objects ordinarily transported in luggage have densities comparable to those of common explosives. As a result, CT baggage scanning in practice also suffers from an undesirable high false alarm rate, leading to the same logistical difficulties as encountered with dual energy inspection systems. Although CT systems are billed as Explosive Detection Systems (EDS), the long inspection times and need for extensive human intervention due to the high false alarm rate compromises their efficiency and effectiveness.

The use of x-ray diffraction, also known as a form of coherent x-ray scattering, has been proposed as an alternative approach to contraband detection. Constructive interference of scattered x-rays occurs when the x-rays emerge from a target at the same angle and are in phase. This occurs when the phase lag between rays in a wave front is an integral number of wavelengths of the x-ray radiation. The condition of an integral number of wavelengths is satisfied for x-rays of wavelength $\lambda$ scattered at an angle $\theta$ from the incident beam direction from a sample having a crystal lattice spacing d, in accordance with the following formula, $$\lambda = 2d \sin(\theta/2). \quad (1)$$

This equation is often known as Bragg's Law.

Most solid materials that are found in nature or are manufactured exist in polycrystalline form. That is, they comprise a large number of tiny, individual grains or crystallites. The atoms within each crystallite are located in regularly spaced positions, which are uniquely characteristic of a given material. These regularly spaced atoms, in turn, define a plurality of crystal lattice spacings uniquely associated with that material. As a result, the set of lattice spacings can serve as a unique fingerprint for that material. Such fingerprints may readily be determined for most ceramics, polymers, explosives, and metals.

The x-ray diffraction or coherent scattering technique is widely practiced for laboratory analysis for identifying unknown materials in a sample. Laboratory x-ray diffraction is most commonly implemented in an angular-resolved form. In its usual form, angular-resolved coherent scattering (AR-CS) comprises illumination of a sample with a narrowly collimated, line or pencil beam of monochromatic x-rays, i.e. x-rays having a wavelength $\lambda$ within a very narrow range. Some of the x-ray flux incident on a sample is coherently scattered in accordance with Bragg's Law. The scattering for a polycrystalline sample comprising an assemblage of a large number of randomly oriented crystallites is concentrated in a series of circular cones, each cone having an apex at the sample and being centered on the incident beam direction and having a half-opening angle of $\theta$. The intensity of this scattered radiation is determined experimentally at a series of values of angle $\theta$. A graph of the scattered intensity versus angle is commonly termed an x-ray diffraction or scattering pattern, and is characterized by a plurality of narrow peaks seen at angles $\theta_i$ for a series of i values. The measured values of $\theta_i$ in turn allow corresponding values of $d_i$, the crystal lattice spacing which gives rise to the i-th diffraction peak, to be calculated from Equation (1). Unknown samples are identified by comparing the set of experimentally-determined lattice spacings $d_i$ with the spacings of known materials. An unknown sample can be conclusively identified if its observed d-spacings match the d-spacings of a known sample with sufficient accuracy.

Less commonly, laboratory diffraction is implemented in an energy-resolved form (ER-CS), in which the sample is illuminated by polychromatic x-ray radiation. A polychromatic source, is one which emits radiation having a spread of energies and wavelengths, in contrast to a monochromatic source, which emits radiation having only a single wavelength and energy. It is known that the wavelength $\lambda$ and the energy E of x-ray photons are connected by the equation:

$$E = hc/\lambda, \quad (2)$$

wherein h is Planck's constant and c is the speed of light. Bragg's law may thus be rewritten in a form more appropriate for ER-CS:

$$(1/2d) = (E/hc)\sin(\theta/2) \quad (3)$$

wherein $\chi = (E/hc)\sin(\theta/2)$ is a quantity conventionally termed momentum transfer. The ER-CS method normally employs an x-ray detector capable of resolving the energy of radiation incident thereon. The detector is positioned at a fixed scattering angle $\theta$ and detects coherently scattered radiation of a range of energies. Bragg's Law is satisfied for certain energies and d-spacings, so the detected radiation spectrum has peaks at these energies.

A material's x-ray diffraction pattern stems directly from its characteristic atomic structure and can thus serve as a unique fingerprint for identifying the material. Therefore, diffraction methods theoretically provide better discrimination and a dramatically lower false alarm rate than either CT or dual energy transmission screening methods. While x-ray diffraction in both forms is routinely practiced as a laboratory analysis method, known systems are complex and require skilled operators to collect and interpret the data. Moreover, the laboratory systems are incapable to carrying out analysis with the speed and reliability required for any practical baggage screening system. Accordingly, x-ray diffraction systems have not received widespread acceptance for baggage screening.

Both angular resolved coherent scatter (AR-CS) and energy resolved coherent scatter (ER-CS) systems have been proposed for baggage screening. Each has advantages and disadvantages. The AR-CS method can be implemented with a relatively simple x-ray detector, instead of a relatively complex and expensive energy-resolved detector. However, the AR-CS method requires a monochromatic x-ray beam, obtained either from the fluorescence of the source anode (most often made of tungsten) or by filtering a polychromatic beam. In either case, the number of x-ray photons available to scatter from the baggage for content analysis is severely limited. Typically, a filter is used to select x-ray photons having energy within a narrow range, e.g. an energy range encompassing the tungsten fluorescence lines near 59 keV. Unfortunately available filters are not perfect and reduce the number of photons of the desired energy. They also transmit extraneous x-rays having energies outside the desired range that muddle the resulting angular spectrum. The net effect of filtering the primary x-ray beam is to increase substantially the time needed to scan the baggage, since most of the x-rays emitted by the x-ray source are attenuated before reaching the luggage and so are not used.

On the other hand, the ER-CS method does not require a filter, and the entire x-ray spectrum potentially can be utilized. The disadvantage is that the detectors must be energy resolving, which makes the detector system more complex and costly. In addition the detector is usually positioned at a fixed angle. Bragg's Law generally is not satisfied for any x-rays in the most intense part of the spectrum, i.e. for energies near the 59 keV peak in the x-ray spectrum flux. As a result, only a small portion of the entire x-ray flux that impinges on the baggage is effectively used, likewise lengthening inspection times.

In particular, the x-ray flux spectrum typically emitted by an x-ray tube having a tungsten anode target and a 2 mm window is depicted by FIG. 10. Some 23% of the flux is contained within the tungsten fluorescence peaks near 59 keV. Additional fluorescence peaks at about 67 keV comprise about 7% of the total flux. At best, AR-CS methods rely on a small minority of the total flux, typically less than even the 23% in the 59 keV peaks. While the ER-CS method utilizes somewhat more of the x-ray flux, a large part of the intensity still cannot effectively use all the flux as a result of limitations inherent in the use of fixed scattering angles.

Methods that combine energy and angular resolution have also been proposed. However, these methods have generally entailed use of a highly collimated, pencil beam of x-rays. While such methods are suggested to be useful in locating contraband within an item, the tight collimation significantly limits the x-ray flux in both intensity and spatial extent, thus slowing the scanning to an undesirable degree.

Previous x-ray methods have also suffered from limitations that result from the techniques used to correct for the non-coherent absorption of x-ray flux traversing the item being interrogated. For example, some systems have employed a sidescattering technique that entails the complexity and expense of an additional detection system.

X-ray scattering methods that efficiently use x-ray flux from a source, while minimizing the exposure of baggage to radiation that is ineffectual in substance identification, are thus highly sought. Desirable methods also afford rapid and sensitive scanning for reliable identification of targeted substances without generation of unwarranted false alarms.

Notwithstanding the aforementioned approaches, there remains a need in the art for systems capable of reliably, accurately, and rapidly detecting the presence of contraband substances, especially explosives, accelerants, and illicit drugs. More particularly, there is need for systems that are readily automated for semi-continuous or continuous inspection and detection of the presence of such materials in luggage, cargo, vehicles, freight containers, and related items. Such systems are highly sought, especially in the context of airport screening, but would be equally valuable for courthouses, stadiums, schools, government offices, military installations, correctional institutions, and other public venues that might be targets of terrorist or similar criminal activity.

SUMMARY OF THE INVENTION

The present invention provides a scanning system that rapidly detects the presence of a wide variety of contraband substances in an accurate, reliable manner. The system rapidly and accurately discriminates among different substances and provides quantitative indication of the amount and location of a critical substance. It is especially well suited for use in applications which require high throughput and accuracy, such as security screening associated with airline and other forms of public transportation.

Advantageously, the system provides for automated screening, in which an interrogation volume within a baggage item is scanned to signal the presence of at least one contraband substance. The interrogation volume may comprise any fraction of the baggage item up to substantially its entire volume. Checked and other hand-carried items of luggage, personal effects, and cargo of any form may be tested, without the need of physical contact by an operator. Vagaries of human performance are virtually eliminated, and detection efficacy is improved. The system's accuracy, reliability, and flexibility, as well as its lower operational cost, and expanded range of detectable substances overcome problems associated with commercial scanning systems. Importantly, the system of this invention markedly reduces or eliminates false alarms while maximizing detection sensitivity for actual contraband.

The system of the invention employs both energy and angle resolved coherent scatter methods (EAR-CS), in which a plurality of energy-resolved (ER-CS) spectra are obtained at different angles (AR-CS). Advantageously, the combined energy and angle resolved system makes efficient use of the flux of x-rays from a source. In a preferred embodiment of the system, the detected, coherently scattered radiation is further increased by the increase in effective detector area resulting from use of plural, simultaneously operative detectors. In addition, the flux contained within the fluorescence peaks of the source results in intense coherent scattering at angles at which the detector system is operative.

Most of the materials encountered in baggage items under investigation are non-uniform and therefore will yield non-uniform results in their individual ER-CS or AR-CS spectra. By collecting combined EAR-CS spectra, these non-uniformities in many instances average out in the combined data set. Beneficially, the EAR-CS system enjoys a higher signal to noise ratio than previous systems, permitting the scan throughput to be increased while maintaining or reducing the false alarm rate and the resulting need for physical inspection by security personnel.

In one aspect of the invention, the EAR-CS scattering technique is employed in conjunction with a pre-scanning device, such as a CT or multiview dual energy system, by which one or more suspect regions of the baggage are located and targeted for more detailed scrutiny. This identification is conveyed to the positioning equipment of the present invention and the EAR-CS scanning for suspect material is concentrated on an identified volume. As a result, the limited scanning time available is used more efficiently by concentrating predominantly on regions most likely to contain contraband.

BRIEF DESCRIPTION OF THE DRAWINGS

The invention will be more fully understood and further advantages will become apparent when reference is had to the following detailed description of the preferred embodiments of the invention and the accompanying drawings, wherein like reference numerals denote similar elements throughout the several views and in which.

DESCRIPTION OF THE PREFERRED EMBODIMENTS

The present invention provides an energy/angle resolved coherent scattering (EAR-CS) system for screening baggage and other articles that employs both energy and angle resolution of coherent scattering data.

Figure 1:
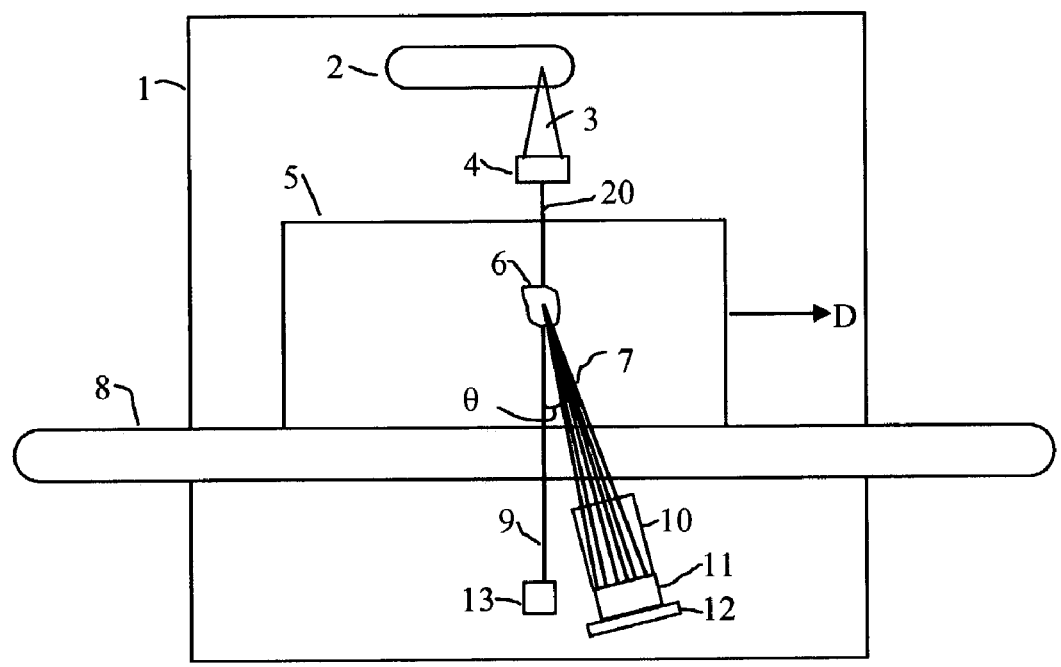
FIG. 1 is a side view of an explosive detection system of the invention adapted to scan selected parts of a baggage item with a full fan beam.
Figure 2:
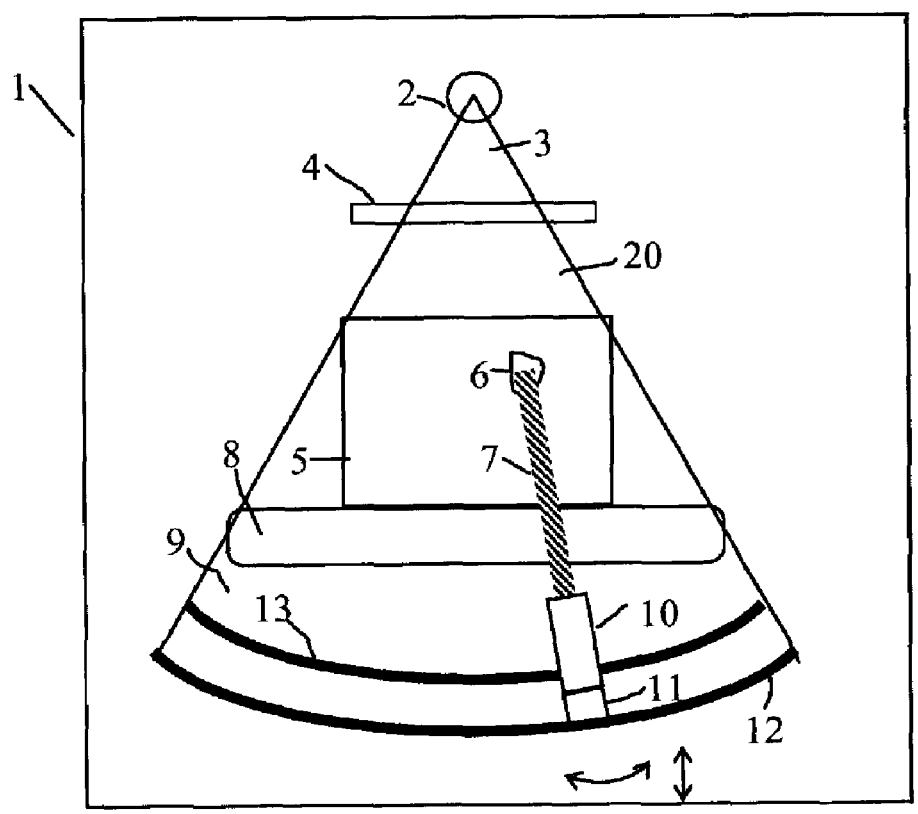
FIG. 2 is a frontal view of the explosive detection system shown in FIG. 1.

Referring now to FIGS. 1–2 there is depicted an embodiment of the invention providing a scanning system for detecting the presence of contraband material within a baggage item. As used herein and in the subjoined claims, the term "contraband" is intended to denote substances or articles whose transportation or possession is forbidden or improper. A wide variety of substances or articles may be considered as contraband, including non-exclusively: firearms and similar weapons; explosives and explosive devices; incendiaries, propellants, and accelerants; drugs such as heroin, cocaine, opium and its derivatives and other narcotics, cannabis (including marijuana and hashish), amphetamines and barbiturates; hallucinogens and psychotropics; and other substances and articles which present biological, chemical or radiological hazards to people and property. The term "baggage item" is intended to include non-exclusively objects such as luggage, suitcases, cargo, freight, boxes, cartons, envelopes, crates, packages, personal articles, and the like, appointed to be hand-carried by an individual or transported on aircraft, rail, ship, bus or other like public conveyance.

Within enclosure 1 depicted by FIGS. 1–2, there is deployed an x-ray source 2 adapted to illuminate an interrogation volume 6 within a baggage item 5, depicted in this instance as a conventional suitcase. Penetrating x-radiation emanating from source 2 in primary beam 3 passes through primary beam collimator 4, which restricts the x-ray flux to a fan beam 20. As used herein and in the subjoined claims, a fan beam is understood to mean a beam that is substantially wider in a first transverse direction perpendicular to the beam direction than in a second transverse direction. Preferably, the beam is about 1 mm wide in its second transverse direction and is at least about 10 times wider in the first direction. Fan beam 20 impinges on volume 6. A portion of the x-ray flux within fan beam 20 is coherently scattered by material within interrogation volume 6, creating a scattered radiation 7. As depicted, interrogation volume 6 is a small part of the total volume of baggage item 5. However, in other embodiments within the scope of the present invention, volume 6 may comprise as much as the entire volume of item 5 and may further comprise the container of item 5 itself. A portion of scattered radiation 7 is intercepted by focusing collimator 10 and passes therethrough to strike energy-resolved detector array 11, which is movably disposed on track 12. A portion of the flux in beam 20 is not scattered and emerges from volume 6 as transmitted beam 9, which strikes dual energy detector array 13. Baggage item 5 is transported through enclosure 1 by motion means, such as a conveyor system 8 of conventional design in a direction indicated by arrow D. The direction of transport is generally perpendicular to the plane containing the width of fan beam 4, i.e., the plane perpendicular to the sheet of FIG. 1 and the plane of the sheet of FIG. 2. Additionally, collimator 10 and detector array 11 are movable along track 12 and in a vertical direction, as indicated by the arrows in FIG. 2, to permit different interrogation volumes within baggage item 5 to be examined.

Figure 3:
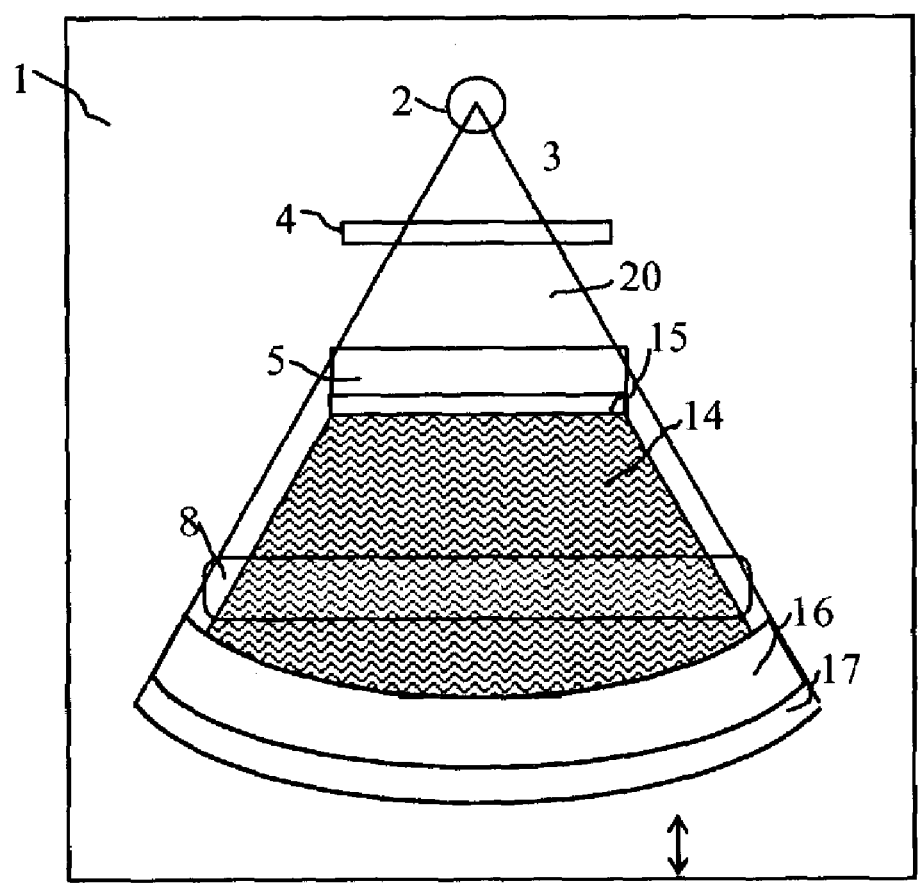
FIG. 3 is a frontal view of another explosive detection system of the invention adapted to scan an entire baggage item with a full fan beam.

FIG. 3 depicts an alternative embodiment in which the interrogation volume 15 comprises substantially the entire volume of baggage item 5 instead of the relatively smaller portion 6 scanned in the embodiment of FIGS. 1–2. Accordingly, the embodiment of FIG. 3 also incorporates focused collimator 16 and energy-resolved detector array 17 that are of greater angular extent than respective collimator 10 and detector 11 seen in FIGS. 1–2.

In other embodiments of the present system, a plurality of energy-resolved detector elements are used instead of the detector array 11 seen in FIG. 1. Advantageously, the use of multiple detector elements permits scattering data to be collected simultaneously at a plurality of scattering angles, in many instances eliminating the need for a mechanical motion means to position the detector at the different angles. Such an arrangement significantly reduces the time needed for data collection, resulting in higher system throughput. Still other embodiments employ one- and two-dimensional, energy-resolved detectors, which are capable of detecting radiation and resolving both its intensity in one or two dimensions, respectively, and its energy.

Any suitable detector having the requisite energy resolution for detecting coherently scattered radiation may be used in the practice of the present invention. These detectors include Ge, CdZnTe (CZT), and CdTe solid state detectors. Preferably, the detector is a CdZnTe or CdTe detector.

The invention further provides a method for scanning an interrogation volume within a baggage item to signal the presence of at least one contraband substance. As best understood by reference to FIGS. 1–2, an implementation of the method comprises illuminating the interrogation volume with a fan beam 20 of penetrating, polychromatic x-ray radiation and detecting the radiation coherently scattered by material within the interrogation volume 6. Preferably, the x-rays are provided by a source such as a conventional, rotating tungsten-anode x-ray tube 2 operating at a potential of about 160 kV. The x-rays pass through a collimating slit 4 to create a fan beam 20 that circumscribes a primary beam direction and has an opening angle preferably ranging from about 40 to 80°. An attenuated portion of fan beam is transmitted along the primary beam direction and impinges on dual energy detector 13. The output of the one or more detectors is used to determine an energy-dependent absorption correction.

The coherently scattered radiation 7 is detected at a plurality of scattering angles θ. At each of the angles, an energy-resolved scattering spectrum is obtained. An energy-resolved scattering spectrum may be represented as a graph of scattered intensity versus x-ray energy. Peaks are seen in the scattering spectrum at certain energy values $E_i$ which correspond to wavelengths $\lambda_i$ by the equation $E_i = hc/\lambda_i$. These $\lambda_i$ values, in turn, satisfy Bragg's Law for various of the lattice d-spacings $d_i$ characteristic of the material within the interrogation volume, as discussed hereinabove.

However, the intensity of the scattering is generally so low that to obtain an adequate signal to noise ratio data must be accumulated for a time that is unacceptably long for a practical baggage screening system. Accordingly, it is preferred that data be accumulated simultaneously in plural detectors and combined to enhance signal to noise ratio for the present analysis.

Figure 4A:
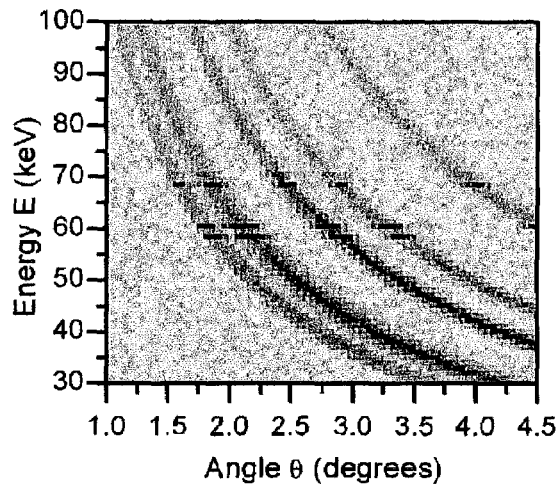
FIG. 4a is a plot of scattered intensity as a function of x-ray energy and scatter angle, obtained in a simulation experiment using a EAR-CS device of the invention with a simulated long data collection (or integration) time resulting in a good signal to noise ratio.
Figure 4C:
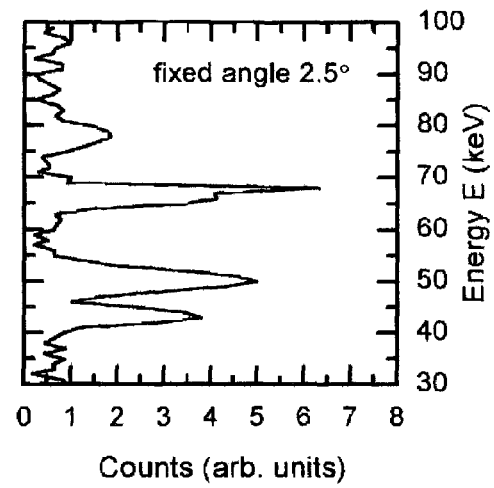
FIG. 4c is a plot of ER-CS derived from FIG. 4a at a constant scattering angle of about 2.5°.
Figure 4B:
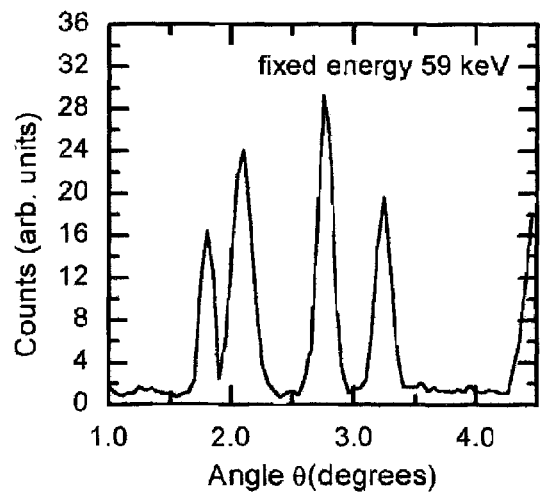
FIG. 4b is a plot of AR-CS derived from FIG. 4a with data representing simulated coherent scattering of monochromatic x-rays having the energy of the tungsten fluorescence line near 59 keV.
Figure 10:
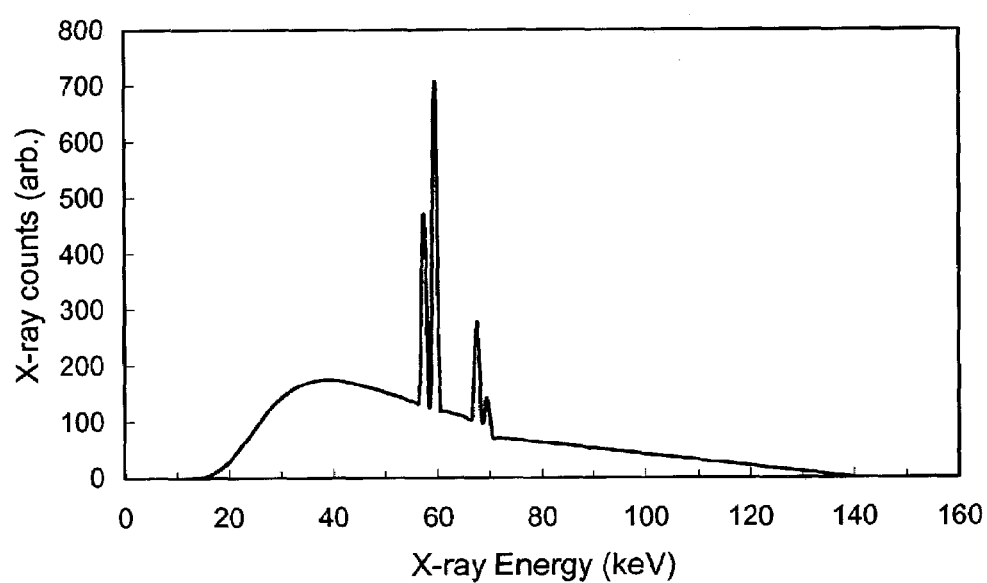
FIG. 10 is a graph depicting the spectrum of x-ray flux emanating from a typical x-ray tube having a tungsten anode.

FIG. 4a depicts the results of a simulation experiment in accordance with the method of the invention, in which computer-generated simulated data are collected for an extended period of time to obtain an acceptable signal to noise ratio. The data are presented in a plot of energy E versus scattering angle θ, the intensity of color or gray scale in the plot representing the intensity of scattered radiation for a hypothetical material. Data of the form seen in FIG. 4a would be collected by a detector with both energy and spatial resolution capability. The five curved bands correspond to five d-spacings $d_i$ or values of momentum transfer $\chi_i$ that satisfy Bragg's Law. The narrow horizontal spots within each band correspond to the energies of the tungsten fluorescence lines at about 59 and 67 keV. As seen in FIG. 10, the incident x-ray flux at these energies is especially high, resulting in intense coherent scattering at these energies. A portion of the data that make up FIG. 4a are extracted to form the graphs seen in FIGS. 4b and 4c, which depict results that would be obtained in AR-CS and ER-CS experiments respectively, conducted using substantially the same conditions. That is to say, the data of FIGS. 4b and 4c represent the results that would be obtained using the same source and the same data collection time using extant AR-CS and ER-CS systems. In particular, FIG. 4b represents a horizontal slice taken across FIG. 4a, i.e. data taken for a constant incident energy of 59 keV, one of the fluorescence energies of tungsten. FIG. 4c represents a vertical slice of FIG. 4a taken at a constant scattering angle of 2.5°. Peaks are clearly perceptible in both FIGS. 4b and 4c.

Figure 6A:
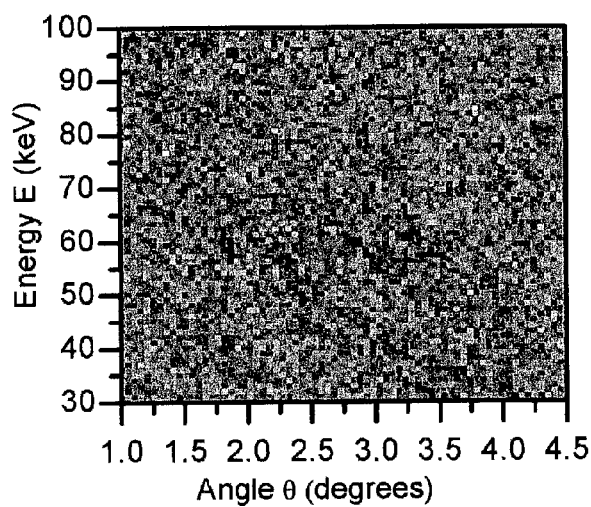
FIG. 6a is a plot of scattered intensity as a function of x-ray energy and scatter angle, obtained in a simulated experiment using an EAR-CS device of the invention with a data collection time sufficiently short for baggage screening and other fast applications.
Figure 6C:
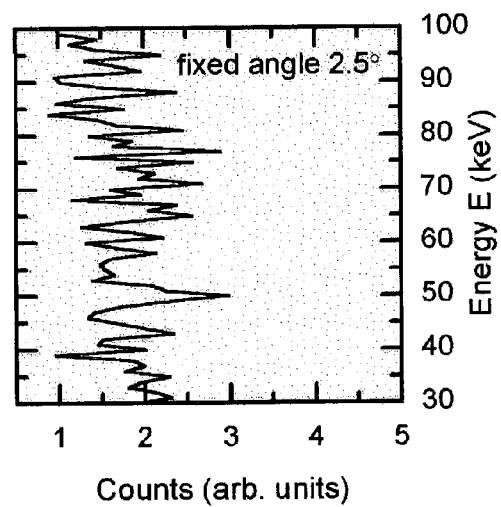
FIG. 6c is a plot of ER-CS derived from FIG. 6a at a constant angle of about 2.5°.
Figure 6B:
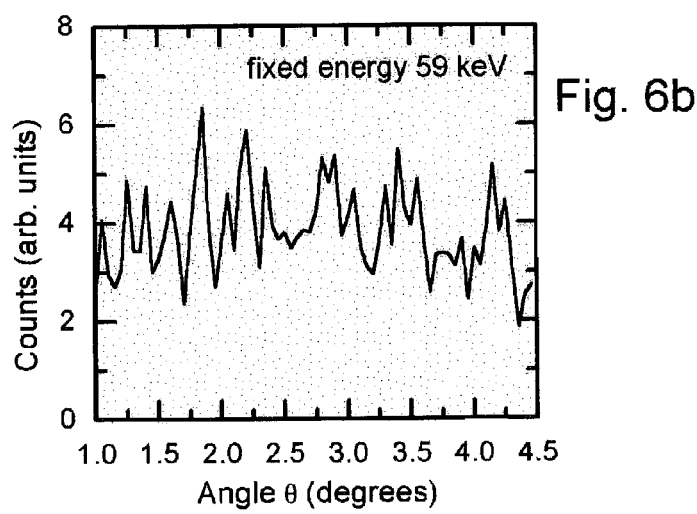
FIG. 6b is a plot of AR-CS derived from FIG. 6a with data representing coherent scattering of monochromatic x-rays having the energy of the tungsten fluorescence line near 59 keV.

However, the data collection time assumed in FIGS. 4a–4c is unacceptably long for a baggage screening system. The same simulated experiment, but with data taken for a much shorter time that would be acceptable for a baggage screening system, results in a much poorer signal to noise ratio, as depicted by FIG. 6a. The bands easily distinguished in FIG. 4a are barely perceptible in FIG. 6a. The slices in FIGS. 6b and 6c, which correspond to FIGS. 4a and 4c, respectively, do not reveal easily discernable peaks.

The present EAR-CS method overcomes the limitations of existing AR-CS and ER-CS systems by simultaneously collecting data resolved in both angle and energy. In the present method, a scattering spectrum is obtained from each of a plurality of scattering angles. Each scattering spectrum corresponds to a vertical slice, such as the data depicted in FIGS. 4c and 6c sliced from the data of FIGS. 4a and 6a, respectively. Each scattering spectrum is then corrected for absorption using a correction derived from a dual energy detection method. The scattering spectra are combined to produce a scattering pattern, which has enhanced signal to noise ratio. In one implementation for combining the spectra, the energy range in each is divided into a plurality of small energy ranges. Each small energy range corresponds to a particular value of momentum transfer $\chi$. The scattering pattern is produced by combining, point by point, the data representing substantially similar values of $\chi$ in the various spectra.

One method for combining the spectra relies on transformation of the scattering angle for each data point to an equivalent, normalized angle $\theta_n$ based on a single energy, such as the maximum energy $E_m$ at which scattering data are collected. The normalized angle $\theta_n$ for scattering of x-rays of energy E at a real angle θ is given by the formula $$\theta_n = 2\sin^{-1}((E/E_m)\sin(\theta/2)). \quad (4)$$

Figure 5A:
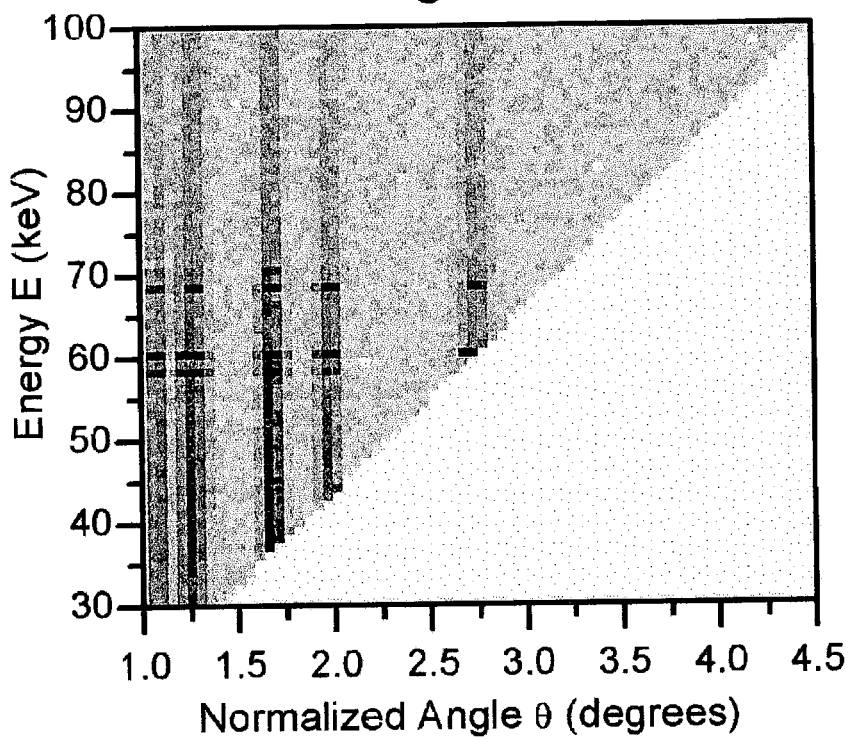
FIG. 5a is an intensity plot of the EAR-CS data from FIG. 4a transformed to a normalized angle as discussed in detail hereinbelow.
Figure 5B:
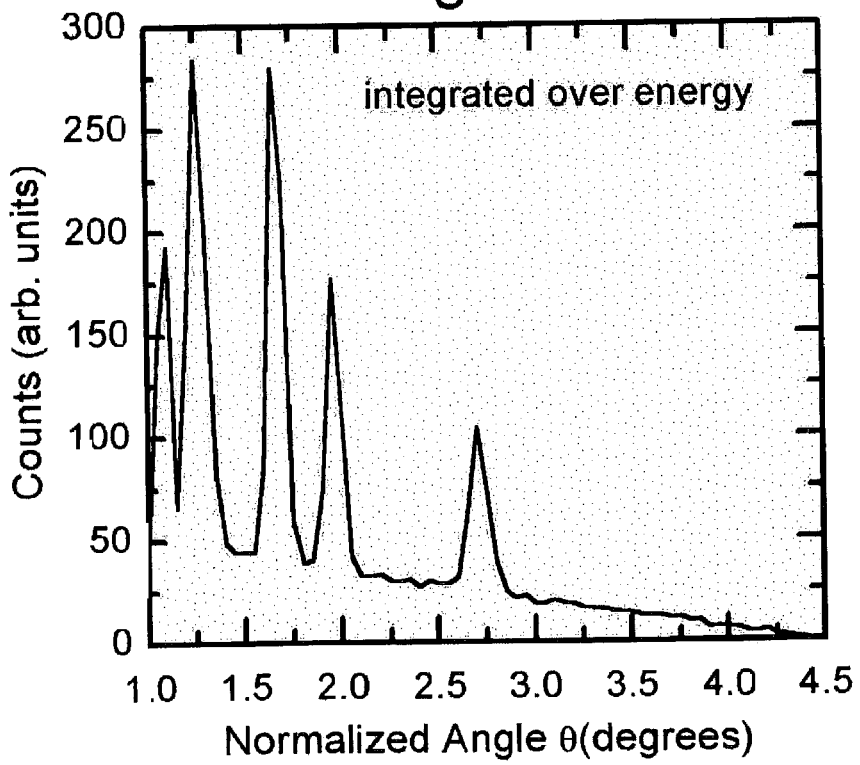
FIG. 5b is a plot of the data in FIG. 5a integrated vertically.

The results of transforming the data of FIG. 4a using Equation (4) are depicted in FIG. 5a. Intensity maxima corresponding to five d-spacings are clearly visible in FIG. 5a. It will be recognized that the data could also be renormalized using a transformation of energy instead of angle. A further summation of the data points of FIG. 5a having substantially the same normalized angles yields the scattering pattern seen in FIG. 5b, in which the intensity maxima of FIG. 5a sum to form the peaks seen in FIG. 5b.

Figure 7A:
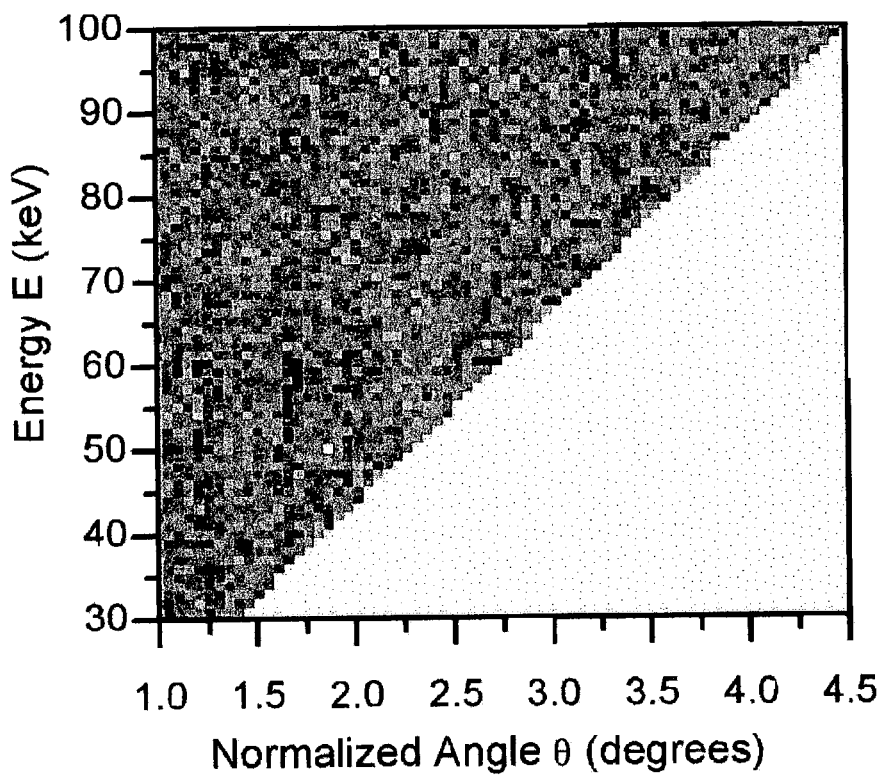
FIG. 7a is an intensity plot of the EAR-CS data of FIG. 6a transformed to a normalized angle as discussed in detail hereinbelow.
Figure 7B:
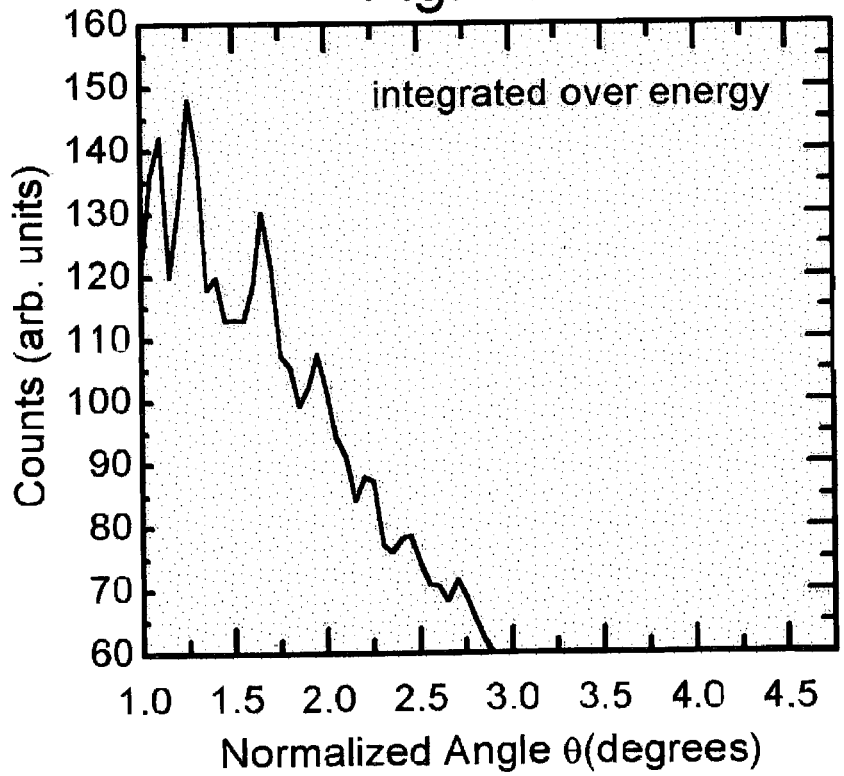
FIG. 7b is a plot of the data in FIG. 7 integrated vertically.

The same transformation of the data of FIG. 6a produces the scattering pattern depicted by FIG. 7a, in which the same peaks are only weakly visible. However, the summation of the points of FIG. 5a having substantially the same normalized angles yields the scattering pattern of FIG. 7b, in which peaks are visible with sufficient signal to noise ratio for a workable baggage scanning system.

An alternate method that yields the same results would be to bin together the results for each constant value of $\chi$ and then prepare a histogram of the resulting data, preferably by using a pre-calculated look-up table that directs each of the pixels in a data set, e.g. those depicted in FIGS. 4a and 6a, to the proper bin locations and adds the pixels in each bin together. Plots of these results also give directly the results set forth in FIGS. 5b and 7b.

Other techniques for combining the scattering spectra to form the combined scattering pattern will be apparent to those skilled in the art and are included within the scope of the present invention.

The method of the invention further comprises comparison of the combined scattering pattern, e.g. as obtained by the foregoing method, with a library of reference scattering patterns. As noted above, every material exhibits a unique scattering pattern, so that detection of an experimental pattern that matches a reference pattern indicates that the sample interrogated contains at least the material corresponding to the reference pattern. In certain instances, it is sufficient to compare the experimental scattering pattern with a single reference pattern to determine the presence or absence of the one corresponding substance. However, in most circumstances the library preferably contains reference scattering patterns characteristic of a large plurality of contraband materials, any one or more of which can thus be detected. The matching of reference and experimental patterns may readily carried out using a computer system programmed to implement pattern matching techniques known in the art.

More specifically, the present EAR-CS method is able to detect the presence of a plurality of substances in an interrogation volume. The presence of multiple substances gives rise to a scattering pattern that is a superposition of the scattering patterns of the individual constituents. That is to say, the experimental scattering pattern exhibits plural peaks, each of which is attributable to one of the substances and occurs at a specific value of $\chi$ that is unaffected by the presence of other substances. In some instances, there may be overlap or coincidence of the peaks of different substances. However, it is extremely unlikely that all the peaks of different substances overlap in a way that precludes identification using the present system.

The present scattering methods are also able to identify semi-crystalline, non-crystalline, amorphous, gels, and other poorly ordered materials in some instances. Many of these materials have sufficient short-range order to produce a scattering pattern having relatively broad peaks with sufficient intensity for detection.

The present method preferably employs a dual energy detection technique to determine an energy-dependent absorption correction. It is known that the intensity of an x-ray beam passing through a uniform material is attenuated exponentially with distance. The extent of attenuation (i.e., the ratio of transmitted to incident flux) is dependent on the thickness and on the atomic density of the material, the average atomic number of the material, and the x-ray energy. In general, the degree of attenuation increases with increasing atomic density and average atomic number but decreases with increasing x-ray energy. For a polychromatic incident beam this attenuation is often termed "beam hardening," since the preferential attenuating of the lower energy portion of the flux increases the average beam energy to a higher value. Higher energy x-rays are often said to be "harder" than lower energy x-rays.

The present dual energy technique preferably relies on two x-ray detectors, one a low energy detector and the other a high energy detector. Systems using either more than two detectors sensitive to different energy ranges or energy-resolved detectors may be useful in some instances as well and are within the scope of the present invention. Preferably, the high and low energy attenuation data are obtained from detectors that are also used in connection with the formation of a dual energy or radiographic density transmission image of the baggage item. Advantageously, additional detectors for collecting the attenuation data are not required with this embodiment. The low energy detector is sensitive to low-energy x-rays but substantially transmissive for high-energy x-rays. In one embodiment, the primary fan beam first passes through the baggage item, then at least part of the beam impinges on the low-energy detector, and subsequently enters the high energy detector. Preferably a filter is interposed between the detectors and serves to strongly attenuate any low energy x-rays that emerge from the low-energy detector. Typically, the systems are sensitive to x-ray energies of about 20 to 80 keV and about 80 to 160 keV, respectively. The system is calibrated, first with no baggage item present to determine the unattenuated flux in both detectors and then with a strongly absorbing sample, e.g. a thick lead sheet, or with the x-ray source deactivated, to determine full attenuation. Preferably, the system is further calibrated with partially attenuating samples of known atomic and mass density and thickness. A range of such samples representative of the items commonly encountered in baggage is preferably used. Such samples typically include Lucite, aluminum, and ferrous metal. Preferably, the samples cover a range of average thickness and average atomic number encompassing the items normally encountered. For each sample and thickness, the fractional attenuation seen in both the low and high energy detectors is determined. Alternatively, the high and low energy attenuations for various reference samples of known atomic number and thickness may be calculated theoretically based on the principles of atomic physics. A lookup table is then developed from which average atomic number and thickness may be inferred for any combination of low and high energy attenuations seen during routine baggage scanning. The ensuing atomic number and thickness values allow an accurate energy-dependent absorption correction to be determined using known principles.

Advantageously, the foregoing dual energy correction is more easily implemented than known correction methods, since the combination of low and high energy fractional attenuations allows both the average atomic number and effective thickness of the sample to be readily determined. It is to be noted that for the small values of scattering angle $2\theta$ normally encountered, i.e. usually less than about 10° and more frequently less than about 5°, the scattered beam traverses a path in the sample that is substantially the same in thickness and composition as in the path of the primary beam.

The lowest order coherent scattering peaks, corresponding to the largest d-spacings of typically encountered materials, are found at scattering angles of less than about 10° for incident x-ray energies of 30–150 keV preferably used in the present system. Lower energy x-rays are insufficiently penetrating to examine typical baggage items, while higher energy x-rays result in very low coherent scattering angles that do not permit the primary and scattered beams to be physically distinguished.

Figure 8:
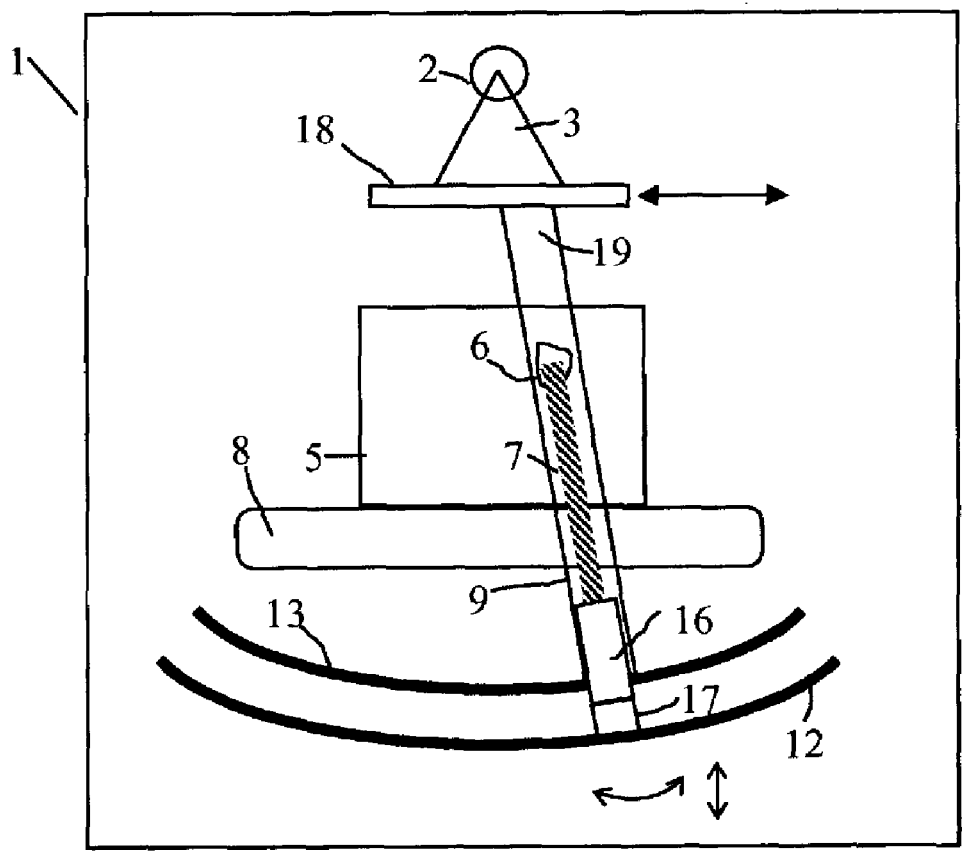
FIG. 8 is a frontal view of an explosive detection system of the invention that scans selected parts of the baggage with a partial fan beam.
Figure 9:
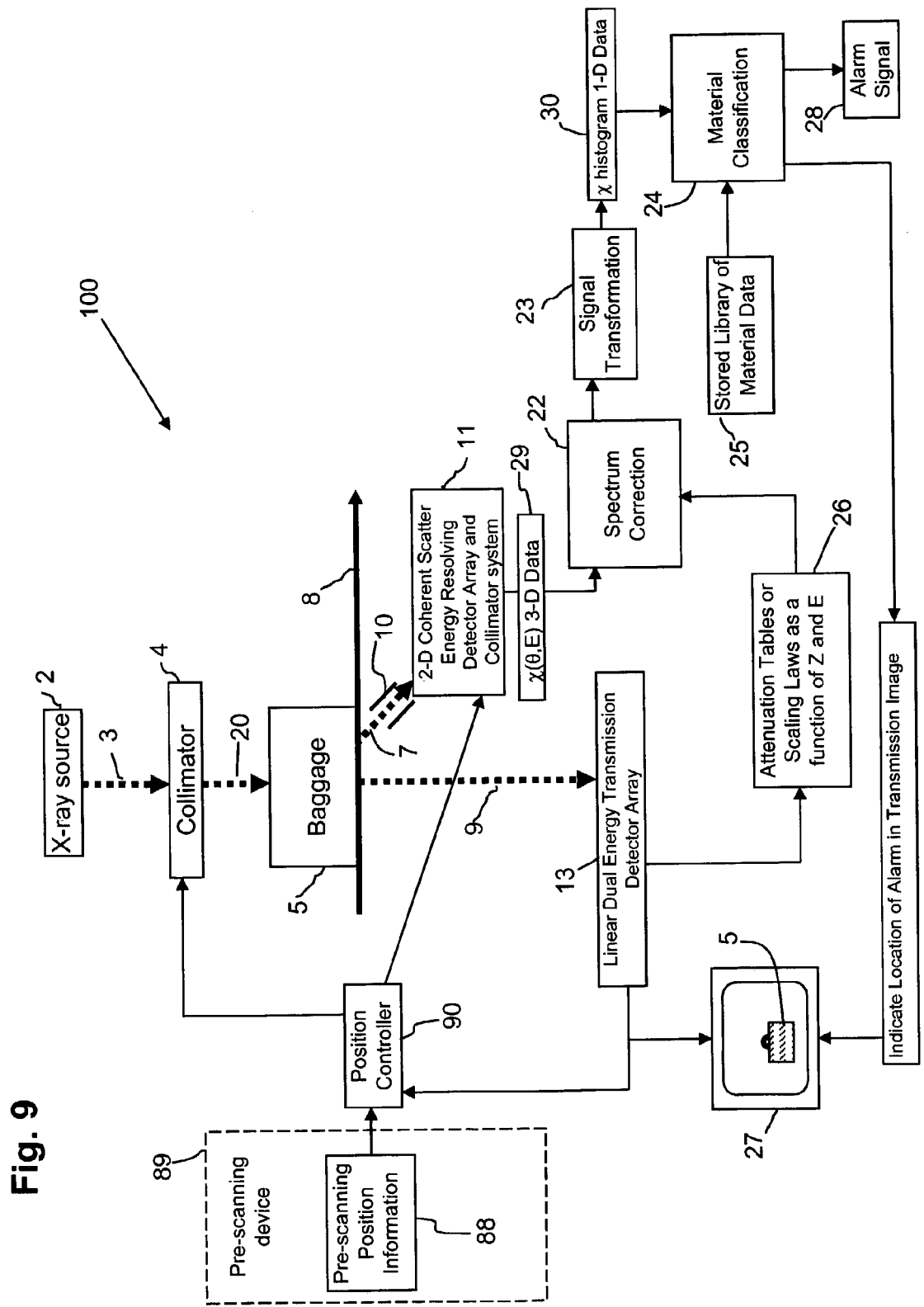
FIG. 9 is a schematic view depicting an implementation of the present method.

Referring now to FIG. 9 there is shown the operation of an embodiment of the present baggage screening system used in conjunction with a prescanning device 89. The system is shown generally at 100. X-ray source 2 produces Bremsstrahlung radiation 3 that is collimated by primary collimator 4 to form fan beam 20 that impinge on baggage item 5. Some of the x-rays are coherently scattered forming the scattered x-ray path 7 and focused onto the 2-D detector array 11 by collimator system 10. Energy-resolved detector system 11 generates signals indicative of the x-rays incident thereon. Signals are recorded based on the scatter angle and the energy of the x-ray photons detected. Preferably, the signals are stored in a data array 29 in the memory of a computer means (not shown), such as a general-purpose computer or specialized digital circuitry incorporated within the detector electronics. An energy-resolved scattering spectrum is constructed from the scattered intensity at each scattering angle. The position of detector system 11, collimator 10, and conveyor 8 are determined from position information 88 from pre-scanning device 89 that determines potential suspect interrogation volume in concert with a position controller 90. Detector system 11 and collimator 10 move in directions indicated by the arrows in FIG. 2 so that any desired volume within baggage 5 can be selected for scanning. Alternatively, a narrow fan beam, such as beam 19 limited by collimator 18 as shown in FIG. 8, may be employed. Use of a narrow fan beam beneficially reduces the likelihood of undesirable multiple scatter events reaching the detector. Some of the x-ray flux either passes through the baggage unaffected undergoes a Compton scatter or photoelectric absorption process. The unaffected flux passes through the baggage item to form beam path 9. This flux is detected by the dual energy detector system 13. In addition dual energy transmission image 27 is constructed by a computer and displayed on display monitor 91.

The atomic number and attenuation information generated from the x-rays collected by dual energy detectors 13 are used in a correction process 22. For example, the scattering spectra may be corrected based on empirically determined attenuation tables or calculated attenuation scaling laws 26 that are a function of the average atomic number and the effective thickness of the material in the beam path and of the x-ray energy. The attenuation information obtained from energy-dependent absorption correction 26 is than used in carrying out correction process 22 that produces corrected spectra data 29.

The corrected data then undergo a signal processing transformation 23 for normalization of the data, e.g. as shown in FIG. 5. The end result of that transformation is a 1-D histogram or scattering pattern 30 of $\chi$. Pattern 30 (FIG. 5.2) is then compared with a library of reference scattering patterns 25 using material classifier function 24, preferably implemented using a computer. If a contraband substance is determined to be in the bag by material classifier 24 an audible or visible alarm signal 28 is generated and the position of the alarm in the baggage is indicated in dual energy transmission image 27. Preferably, a single general purpose computer with a stored computer program is readily used to store the data accumulated during the operations of the present system and to perform the various required data calculations and transformations.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. A system for screening an interrogation volume within a baggage item for the presence of at least one contraband substance, the system comprising:
   a. an x-ray source adapted to emit penetrating, polychromatic radiation;
   b. a primary beam collimator adapted to limit the radiation emanating from said x-ray source to a primary fan beam that opens at a fan angle, circumscribes a primary beam direction, and is incident on said interrogation volume;
   c. a dual-energy detection system, comprising at least a low-energy x-ray detector and a high-energy x-ray detector, each detector being positioned to intercept and detect radiation in said primary fan beam transmitted through said baggage item;
   d. an energy-resolved x-ray detector for detecting radiation coherently scattered from said primary fan beam at a plurality of scattering angles by material within said interrogation volume, material in each portion of said interrogation volume producing scattered radiation detected at each of said plurality of scattering angles;
   e. computer means operably associated with said dual-energy detection system and said energy-resolved x-ray detector, said computer means being adapted to:
      i. determine an energy-dependent absorption correction from the output of said dual-energy detection system;
      ii. produce an energy-resolved scattering spectrum for each of said scattering angles from the output of said energy-resolved x-ray detector;
      iii. correct each of said energy-resolved scattering spectra using said energy-dependent absorption correction to produce a corrected spectrum for each of said scattering angles;
      iv. combine said corrected spectra to produce a diffraction scattering pattern; and
      v. compare said diffraction scattering pattern with the reference diffraction scattering pattern of at least one known contraband substance stored in said computer means to detect a match indicative of the presence of said known contraband substance in said interrogation volume; and
   f. a signal means associated with said computer means, said signal means being activated in response to the detection of said match.

2. A system as recited by claim 1, further comprising a display monitor and wherein said computer means is further adapted to assemble a transmission image of at least a portion of said baggage item using data generated by said dual-energy detection system and to display said transmission image on said display monitor.

3. A system as recited by claim 2, wherein said display monitor is adapted to display a mapping indicative of the locations in said baggage item at which a contraband substance has been detected.

4. A system as recited by claim 3, wherein said mapping is a false color mapping superimposed on said transmission image.

5. A system as recited by claim 1, wherein said energy-resolved x-ray detector is selected from the group consisting of Ge, CdTe, and CdZnTe detectors.

6. A system as recited by claim 5, wherein said energy-resolved x-ray detector is one of a CdTe or CdZnTe detector.

7. A system as recited by claim 1, wherein said energy-resolved x-ray detector is a two-dimensional, energy and position-resolved detector.

8. A system as recited by claim 1, comprising a plurality of energy-resolved x-ray detectors, each disposed at a separate scattering angle.

9. A system as recited by claim 1, further comprising motion means for relatively moving said baggage item and said fan beam, whereby said penetrating radiation is incident on an extended interrogation zone.

10. A system as recited by claim 9, wherein said motion means comprises a conveyor belt for moving said baggage item.

11. A system as recited by claim 1, further comprising a focusing collimator adapted to intercept said coherently scattered radiation and pass said radiation to said energy-resolved x-ray detector.

12. A method for scanning an interrogation volume within a baggage item to signal the presence of at least one contraband substance, comprising the steps of:
   a. illuminating said interrogation volume with a primary fan beam of penetrating, polychromatic radiation, said fan beam opening at a fan angle and circumscribing a primary beam direction;
   b. determining an energy-dependent absorption correction for radiation transmitted through said interrogation volume using dual-energy detection;
   c. detecting, at a plurality of scattering angles, radiation coherently scattered by material within said interrogation volume to produce an energy-resolved scattering spectrum for each of said scattering angles, said detecting comprising use of at least one energy-resolved x-ray detector and material in each portion of said interrogation volume producing scattered radiation detected at each of said plurality of scattering angles;
   d. correcting each of said scattering spectra for absorption using said energy-dependent absorption correction to produce a corrected spectrum for each of said scattering angles;
   e. combining said corrected spectra to produce a diffraction scattering pattern;
   f. comparing said diffraction scattering pattern with at least one reference diffraction scattering pattern of a known contraband substance to detect a match indicative of the presence of said known contraband substance in said interrogation volume; and
   g. activating a signal means in response to the detection of said match.

13. A method as recited by claim 12, said determination of said energy-dependent absorption correction comprises measuring the attenuation of said primary fan beam by said baggage item at a plurality of energies.

14. A method as recited by claim 13, said determination of said energy-dependent absorption correction further comprising the steps of:
   a. determining the reference attenuation of a plurality of reference samples of known reference average atomic number and reference thickness;

b. interpolating an average sample atomic number and average thickness representative of said interrogation volume from a comparison of said measured attenuation with said reference attention of said reference samples; and c. calculating the energy dependent absorption of material having said average sample atomic number and average thickness.

15. A method as recited by claim 13, further comprising the steps of assembling a transmission image of at least a portion of said baggage item using said dual energy detection and displaying said transmission image on a display monitor.

16. A method as recited by claim 15, wherein visual indication of said match is superimposed on said transmission image.

17. A method as recited by claim 15, wherein said interrogation volume is selected using said transmission image.

18. A method as recited by claim 12, wherein substantially all the volume of said baggage item is scanned.

19. A method as recited by claim 12, wherein said detector is selected from the group consisting of Ge, CdTe, and CdZnTe detectors.

20. A method as recited by claim 19, wherein said detector is one of a CdTe and CdZnTe detector.

21. A method as recited by claim 12, wherein said detector is a two-dimensional, energy and position-resolved detector.

22. A method as recited by claim 12, wherein detecting step is accomplished with a plurality of said energy-resolved detectors, each disposed at a separate scattering angle.

23. A method as recited by claim 12, wherein said scanning is carried out by a computer program operably stored in a computer.

24. A method as recited by claim 12, wherein said penetrating, polychromatic radiation is produced by an x-ray tube.

25. A method as recited by claim 24, wherein said x-ray tube comprises a tungsten anode and operates at a potential of at least about 160 kV.

26. A method as recited by claim 12, wherein said detecting step comprises use of a focusing collimator adapted to intercept said coherently scattered radiation and pass said radiation to said at least one energy-resolved x-ray detector.

* * * * *